US008506520B2

(12) United States Patent  (10) Patent No.: US 8,506,520 B2
Kahle et al.  (45) Date of Patent: Aug. 13, 2013

(54) TROCAR SYSTEM WITH LAPAROSCOPE GAS CHANNEL

(75) Inventors: Henry Kahle, Trabuco Canyon, CA (US); Arkadiusz Strokosz, Dana Point, CA (US); Scott V. Taylor, Mission Viejo, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 742 days.

(21) Appl. No.: 12/569,652

(22) Filed: Sep. 29, 2009

(65) Prior Publication Data

US 2010/0081988 A1  Apr. 1, 2010

Related U.S. Application Data

(60) Provisional application No. 61/101,061, filed on Sep. 29, 2008.

(51) Int. Cl.
*A61M 37/00* (2006.01)

(52) U.S. Cl.
USPC .......................................................... 604/23

(58) Field of Classification Search
USPC .................................... 604/23, 264; 606/190
See application file for complete search history.

(56) References Cited

U.S. PATENT DOCUMENTS

| RE682 E | 4/1859 | Peale |
|---|---|---|
| 207,932 A | 9/1878 | Alvord |
| 396,754 A | 1/1889 | Mayfield |
| 1,147,408 A | 7/1915 | Kells |
| 1,727,495 A | 9/1929 | Wappler |
| 1,845,727 A | 2/1932 | Slaughter |

(Continued)

FOREIGN PATENT DOCUMENTS

| DE | 0365049 | 12/1922 |
|---|---|---|
| DE | 1616107 | 4/1972 |

(Continued)

OTHER PUBLICATIONS

The International Searching Authority, The International Search Report and the Written Opinion for International Application No. PCT/US2009/058792, mailed Dec. 23, 2009, entitled "First Entry Trocar System".

(Continued)

*Primary Examiner* — Kevin C Sirmons
*Assistant Examiner* — Bradley Osinski
(74) *Attorney, Agent, or Firm* — Rimas T. Lukas; Pui Tong Ho (57) ABSTRACT

A surgical access system comprises a trocar, an insufflating optical obturator slidably insertable into the trocar, and a laparoscope slidably insertable into the obturator. A distal end of the obturator comprises a tip, at least a portion of which comprises a wall with a generally uniform thickness comprising a transparent material. At least one vent hole disposed at the obturator tip is fluidly connected to a gas flow channel defined by an interior surface of the obturator and the laparoscope, which is fluidly connected to an insufflation gas inlet disposed at a proximal end of the trocar. Improved optical characteristics of the trocar system permit precise and accurate visual placement thereof into a body cavity. Accordingly the access system is suitable as a first entry surgical access system. Embodiments of the trocar access are also useful for drug delivery, and/or for fluid and/or tissue aspiration.

22 Claims, 8 Drawing Sheets

(56) References Cited

U.S. PATENT DOCUMENTS

| | | |
|---|---|---|
| 2,102,274 A | 12/1937 | Larimore |
| 2,699,770 A | 1/1955 | Fourestier et al. |
| 2,932,294 A | 4/1960 | Fourestier et al. |
| 3,021,834 A | 2/1962 | Sheldon |
| 3,042,022 A | 7/1962 | Sheldon |
| 3,224,320 A | 12/1965 | Knudsen |
| 3,279,460 A | 10/1966 | Sheldon |
| 3,357,433 A | 12/1967 | Fourestier et al. |
| 3,417,745 A | 12/1968 | Sheldon |
| 3,437,747 A | 4/1969 | Sheldon |
| 3,459,189 A | 8/1969 | Alley et al. |
| 3,556,085 A | 1/1971 | Takahashi |
| 3,613,684 A | 10/1971 | Sheridan |
| 3,653,338 A | 4/1972 | Sauey |
| 3,821,956 A | 7/1974 | Gordhamer |
| 3,870,036 A | 3/1975 | Fiore |
| 3,961,621 A | 6/1976 | Northeved |
| 3,994,287 A | 11/1976 | Turp |
| 4,112,932 A | 9/1978 | Chiulli |
| 4,180,068 A | 12/1979 | Jacobsen et al. |
| 4,191,191 A | 3/1980 | Auburn |
| 4,222,375 A | 9/1980 | Martinez |
| 4,248,214 A | 2/1981 | Hannah et al. |
| 4,254,762 A | 3/1981 | Yoon |
| 4,269,192 A | 5/1981 | Matsuo |
| 4,299,230 A | 11/1981 | Kubota |
| 4,311,138 A | 1/1982 | Sugarman |
| 4,319,563 A | 3/1982 | Kubota |
| 4,356,826 A | 11/1982 | Kubota |
| 4,429,856 A | 2/1984 | Jackson |
| 4,436,519 A | 3/1984 | O'Neill |
| 4,493,444 A | 1/1985 | Dell Bon et al. |
| 4,498,902 A | 2/1985 | Ash et al. |
| 4,524,805 A | 6/1985 | Hoffman |
| 4,535,773 A | 8/1985 | Yoon |
| 4,535,808 A | 8/1985 | Johanson et al. |
| 4,537,593 A | 8/1985 | Alchas |
| 4,567,882 A | 2/1986 | Heller |
| 4,601,710 A | 7/1986 | Moll |
| 4,779,613 A | 10/1988 | Hashiguchi et al. |
| 4,850,393 A | 7/1989 | Lashomb |
| 4,895,431 A | 1/1990 | Tsujiuchi et al. |
| 4,901,142 A | 2/1990 | Ikuno et al. |
| 4,972,827 A | 11/1990 | Kishi et al. |
| 5,030,210 A | 7/1991 | Alchas |
| 5,057,082 A | 10/1991 | Burchette, Jr. |
| 5,066,288 A | 11/1991 | Deniego et al. |
| 5,098,388 A | 3/1992 | Kulkashi et al. |
| 5,104,388 A | 4/1992 | Quackenbush |
| 5,147,376 A | 9/1992 | Pianetti |
| 5,159,920 A | 11/1992 | Condon et al. |
| 5,163,941 A | 11/1992 | Garth et al. |
| 5,217,441 A | 6/1993 | Shichman |
| 5,246,425 A | 9/1993 | Hunsberger et al. |
| 5,250,068 A | 10/1993 | Ideguchi et al. |
| 5,256,149 A | 10/1993 | Banik et al. |
| 5,269,316 A | 12/1993 | Spitalny |
| 5,271,380 A | 12/1993 | Riek et al. |
| 5,279,567 A | 1/1994 | Ciaglai et al. |
| 5,290,276 A | 3/1994 | Sewell |
| 5,300,033 A | 4/1994 | Miller |
| 5,334,150 A | 8/1994 | Kaali |
| 5,380,291 A | 1/1995 | Kaali |
| 5,389,077 A | 2/1995 | Melinyshyn et al. |
| 5,391,153 A | 2/1995 | Haber |
| 5,392,766 A | 2/1995 | Masterson et al. |
| 5,431,151 A * | 7/1995 | Riek et al. ............... 600/104 |
| 5,441,041 A | 8/1995 | Sauer et al. |
| 5,445,615 A | 8/1995 | Yoon et al. |
| 5,542,845 A | 8/1996 | Jenkins |
| 5,549,546 A * | 8/1996 | Schneider et al. ............... 604/26 |
| 5,569,291 A | 10/1996 | Privitera |
| 5,569,292 A | 10/1996 | Scwemberger et al. |
| 5,609,562 A | 3/1997 | Kaali |
| 5,613,954 A | 3/1997 | Nelson et al. |
| 5,630,805 A | 5/1997 | Ternamian |
| 5,658,236 A | 8/1997 | Sauer |
| 5,662,673 A | 9/1997 | Kieturakis |
| 5,676,611 A | 10/1997 | Foster |
| 5,685,820 A | 11/1997 | Riek et al. |
| 5,720,761 A | 2/1998 | Kaali |
| 5,738,628 A | 4/1998 | Sierocuk et al. |
| 5,752,970 A | 5/1998 | Yoon et al. |
| 5,779,697 A | 7/1998 | Glowa et al. |
| 5,779,967 A | 7/1998 | Hull |
| 5,785,693 A | 7/1998 | Halning |
| 5,792,112 A | 8/1998 | Hart et al. |
| 5,797,888 A | 8/1998 | Yoon et al. |
| 5,797,944 A | 8/1998 | Nobles et al. |
| 5,836,957 A | 11/1998 | Schulz |
| 5,842,971 A | 12/1998 | Yoon |
| 5,860,996 A | 1/1999 | Urban et al. |
| 5,891,013 A | 4/1999 | Thompson |
| 5,893,865 A | 4/1999 | Swindle |
| 5,904,699 A | 5/1999 | Schwemberger et al. |
| 5,924,452 A | 7/1999 | Szpapa et al. |
| 5,957,884 A | 9/1999 | Hooven |
| 5,968,060 A | 10/1999 | Kellogg |
| 5,976,168 A | 11/1999 | Chin |
| 6,001,084 A | 12/1999 | Riek et al. |
| 6,007,481 A | 12/1999 | Riek et al. |
| 6,053,194 A | 4/2000 | Nelson et al. |
| 6,092,551 A | 7/2000 | Bennett |
| 6,228,063 B1 | 5/2001 | Aboul-osn |
| 6,387,043 B1 | 5/2002 | Yoon |
| 6,508,759 B1 | 1/2003 | Taylor et al. |
| 6,520,939 B2 | 2/2003 | Lafontaine |
| 6,656,160 B1 | 12/2003 | Taylor et al. |
| 6,685,630 B2 | 2/2004 | Sauer et al. |
| 6,887,194 B2 | 5/2005 | Hart et al. |
| 7,037,303 B2 | 5/2006 | Beaufore et al. |
| 7,056,294 B2 | 6/2006 | Khairkhahan et al. |
| 2002/0183715 A1 | 12/2002 | Mantell et al. |
| 2003/0023201 A1 | 1/2003 | Aboul-Hosn et al. |
| 2003/0187471 A1 | 10/2003 | Cooper |
| 2004/0082969 A1 | 4/2004 | Kerr |
| 2004/0093000 A1 | 5/2004 | Kerr |
| 2004/0106942 A1 | 6/2004 | Taylor et al. |
| 2004/0204671 A1 | 10/2004 | Stubbs et al. |
| 2004/0230155 A1 | 11/2004 | Blanco et al. |
| 2004/0254517 A1 | 12/2004 | IQuiroz-Mercado et al. |
| 2005/0149094 A1 | 7/2005 | Kasahara et al. |
| 2005/0159711 A1 | 7/2005 | Kathrani et al. |
| 2005/0216028 A1 | 9/2005 | Hart et al. |
| 2005/0227610 A1 | 10/2005 | Zukor et al. |
| 2005/0283122 A1 | 12/2005 | Nordgren |
| 2005/0288622 A1 * | 12/2005 | Albrecht et al. ............... 604/23 |
| 2006/0118189 A1 | 6/2006 | Tekulve et al. |
| 2007/0075465 A1 | 4/2007 | Taylor et al. |
| 2008/086074 A1 | 4/2008 | Taylor et al. |

FOREIGN PATENT DOCUMENTS

| | | |
|---|---|---|
| DE | 2218901 | 10/1973 |
| DE | 2538758 | 3/1977 |
| DE | 29 29 233 | 1/1980 |
| DE | 2922239 | 12/1980 |
| DE | 4020956 | 1/1991 |
| DE | 4133073 | 4/1992 |
| DE | 4035146 | 5/1992 |
| DE | 4116648 | 11/1992 |
| EP | 0135364 | 3/1985 |
| EP | 0312787 | 4/1989 |
| EP | 0347140 | 12/1989 |
| EP | 0369936 | 5/1990 |
| EP | 0369937 | 5/1990 |
| EP | 0474124 | 3/1992 |
| EP | 0724864 | 8/1996 |
| FR | 1370580 | 8/1964 |
| SU | 942730 | 7/1982 |
| SU | 1328658 | 8/1987 |
| SU | 1329769 | 8/1987 |
| WO | WO 97/40758 | 11/1997 |
| WO | WO 01/08563 | 2/2001 |

OTHER PUBLICATIONS

Co-Pending U.S. Appl. No. 10/489,403, filed Mar. 11, 2004; Title: Bladeless Obturator.
Co-Pending U.S. Appl. No. 10/514,313, filed Nov. 12, 2004; Title: Blunt Tip Obturator.
Co-Pending U.S. Appl. No. 11/170,567, filed Jun. 29, 2005; Title: Insufflating Optical Surgical Instrument.
Co-Pending U.S. Appl. No. 10/745,262, filed Dec. 23, 2003, Title: Catheter With Conduit Traversing Tip.
Co-Pending U.S. Appl. No. 10/956,167, filed Oct. 3, 2003; Title: Bladeless Optical Obturator.
Co-Pending U.S. Appl. No. 10/346,846, filed Jan. 17, 2003; Title: Surgical Access Apparatus and Method.
Co-Pending U.S. Appl. No. 10/805/864, filed Mar. 22, 2004; Title: Surgical Access Port and Method.
Co-Pending U.S. Appl. No. 11/868,883, filed Oct. 8, 20007; Title Visual Insufflation Port.
International Searching Authority, The International Search Report and Written Opinion of the International Searching Authority for International Application No. PCT/US2007/080724 mailed Apr. 16, 2008.
International Preliminary Report of Patentability for international application No. PCT/US2005/022716, mailed Jan. 18, 2007.
European Patent Office, The International Search Report and Written Opinion for International Application No. PCT/US2005/022716, mailed Nov. 22, 2005.
The International Bureau of WIPO, The International Preliminary Report on Patentability for International Application No. PCT/US2009/058792, issued Mar. 29, 2011.

* cited by examiner

TROCAR SYSTEM WITH LAPAROSCOPE GAS CHANNEL

CROSS REFERENCE TO RELATED APPLICATION

This application claims the benefit of U.S. Application No. 61/101,061, filed Sep. 29, 2008, the entire disclosure of which is incorporated by reference.

BACKGROUND

1. Technical Field

This disclosure is generally directed to surgical access devices, and more particularly, to a first-entry surgical access system.

2. Description of the Related Art

Trocars are used for instrument access to body cavities in minimally invasive surgery, for example, laparoscopic surgery. In laparoscopic surgery of the organs of the abdomen, the abdomen is typically inflated or insufflated with an insufflation gas, for example, carbon dioxide, which lifts the abdominal wall away from the internal organs, thereby facilitating access to the organs, a condition referred to as pneumoperitoneum. Inserting trocars into an abdomen under pneumoperitoneum is relatively easy. Because the abdominal wall is distended away from the internal organs by the pressure of the insufflation gas, inadvertent damage to the organs during insertion is reduced. Before pneumoperitoneum is established, however, the abdominal wall through which the trocar is to be inserted contacts the internal organs directly. Consequently, inserting the first trocar, referred to as first entry, carries an increased risk of damaging the internal organs directly beneath the entry point.

SUMMARY OF THE INVENTION

A surgical access system comprises a trocar, an insufflating optical obturator slidably insertable into the trocar, and a laparoscope slidably insertable into the obturator. A distal end of the obturator comprises a tip, at least a portion of which comprises a wall with a generally uniform thickness comprising a transparent material. At least one vent hole disposed at the obturator tip is fluidly connected to a gas flow channel defined by an interior surface of the obturator and the laparoscope, which is fluidly connected to an insufflation gas inlet disposed at a proximal end of the trocar. Improved optical characteristics of the trocar system permit precise and accurate visual placement thereof into a body cavity. Accordingly the access system is suitable as a first entry surgical access system. Embodiments of the trocar access are also useful for drug delivery, and/or for fluid and/or tissue aspiration.

Some embodiments provide a bladeless trocar that permits visualization of body tissue fibers as they are being separated, thereby permitting a controlled traversal across a body wall. Some embodiments provide a bladeless trocar that accommodates a conventional laparoscope. Some embodiments provide a trocar that enables insufflation of a body cavity and contemporaneous visualization thereof through the distal tip of the obturator.

Some embodiments provide a surgical access system comprising: a tubular trocar comprising a longitudinal axis, a proximal end, a distal end, an elongate cannula, and a seal assembly disposed at a proximal end of the cannula; an insufflating obturator slidably insertable into the trocar, the obturator comprising a longitudinal axis, a proximal end, a distal end, a tubular shaft, a tip disposed at the distal end of the shaft, at least one vent hole disposed on the tip, and a handle disposed at the proximal end of the shaft; and a fluid inlet disposed at a proximal end of the access system. At least a portion of the obturator tip comprises a wall comprises a transparent material with a substantially uniform thickness, the obturator slidably receives a laparoscope into the obturator shaft, and an interior surface of the obturator shaft and tip, and an outer surface of an inserted laparoscope together define a insufflation gas flow channel fluidly connecting the at least one vent hole to the fluid inlet.

In some embodiments, the seal assembly comprises a septum seal and a duckbill valve.

In some embodiments, the fluid inlet is disposed on the proximal end of the trocar.

In some embodiments, the obturator tip is bladeless. In some embodiments, the wall of the obturator tip is not greater than about 0.65 mm thick. In some embodiments, the obturator tip has a substantially uniform wall thickness. In some embodiments, the obturator shaft and tip are unitary. In some embodiments, the obturator tip comprises at least one of polymer, polycarbonate, polysulfone, PEEK, polyether block amide (PEBAX®), polyester, copolyester, and acrylic.

In some embodiments, the obturator tip comprises a single vent hole. In some embodiments, the at least one vent hole is at least one of circular, oval, elliptical, tear-drop shaped, slot shaped, slit shaped, chevron shaped, triangular, rectangular, rhomboid, and polygonal.

Some embodiments further comprise a depth indicator on the obturator tip. In some embodiments, the depth indicator comprises at least one of indicia disposed in a bore of the at least one vent hole, and indicia disposed proximate to the at least one vent hole.

In some embodiments, the obturator further comprises at least one laparoscope stop disposed on at least one of the interior surface of the obturator tip and the interior surface of the obturator shaft. In some embodiments, the interior surface of the obturator tip comprises a non-circular transverse cross section.

In some embodiments, the obturator accommodates laparoscopes with varying diameters. In some embodiments, the obturator tip accommodates a distal end of the laparoscope.

In some embodiments, at least one opening perforates the obturator shaft.

In some embodiments, a cross-sectional area of the insufflation gas flow channel is at least about 1.6 mm$^2$. In some embodiments, a flow rate through the access system is at least about 3.5 L/min at an insufflator setting of about 1.6-2 KPa.

Some embodiments further comprise a laparoscope.

Some embodiments further comprise at least one of a gas flow indicator, an audible gas flow indicator, and a visual gas flow indicator.

Some embodiments provide a method for accessing a targeted body region, the method comprising: inserting a laparoscope into the surgical access system, wherein the obturator is inserted into the trocar; contacting the obturator tip with a body wall; advancing access system through the body wall; observing a position of the obturator tip through the laparoscope; and terminating advancement of the trocar system when the obturator tip is observed to reach a targeted body region.

In some embodiments, the targeted body region is a body cavity.

In some embodiments, observing the position of the obturator tip comprises observing the position of the at least one vent hole.

Some embodiments further comprise coupling the gas inlet of the surgical access system to a source of insufflation gas.

Some embodiments further comprise at least one of delivering a medicament through the at least one vent hole to the targeted body region; delivering a fluid; aspirating a fluid; and withdrawing tissue.

Some embodiments further comprise removing the obturator from the trocar.

DETAILED DESCRIPTION OF CERTAIN EMBODIMENTS

Figure 1A:
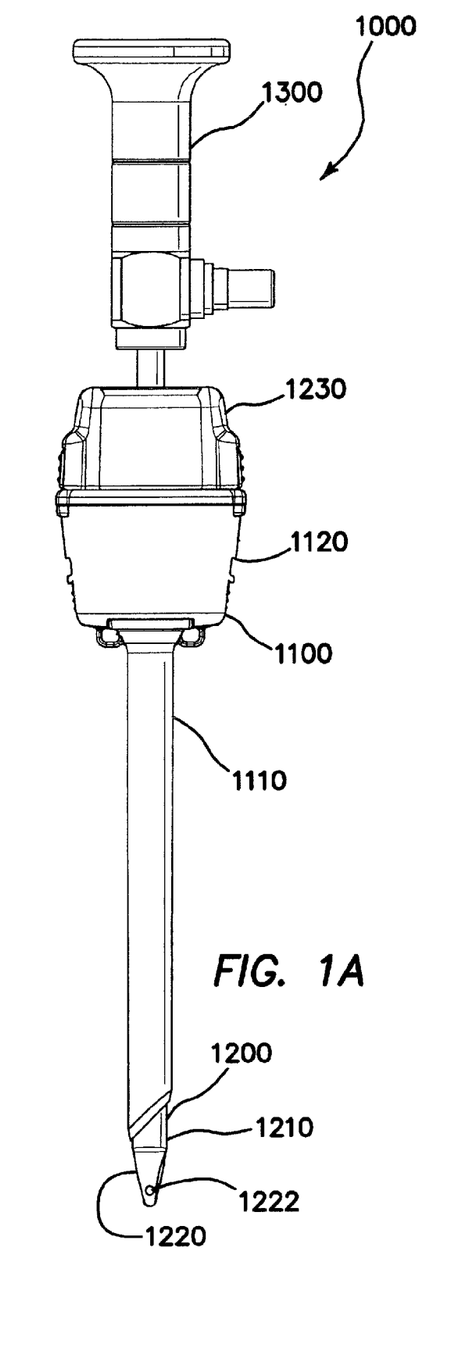
FIG. 1A is a front view and FIG. 1B is a side view of an embodiment of a surgical access system comprising a trocar, an insufflating optical obturator, and a laparoscope.
Figure 1B:
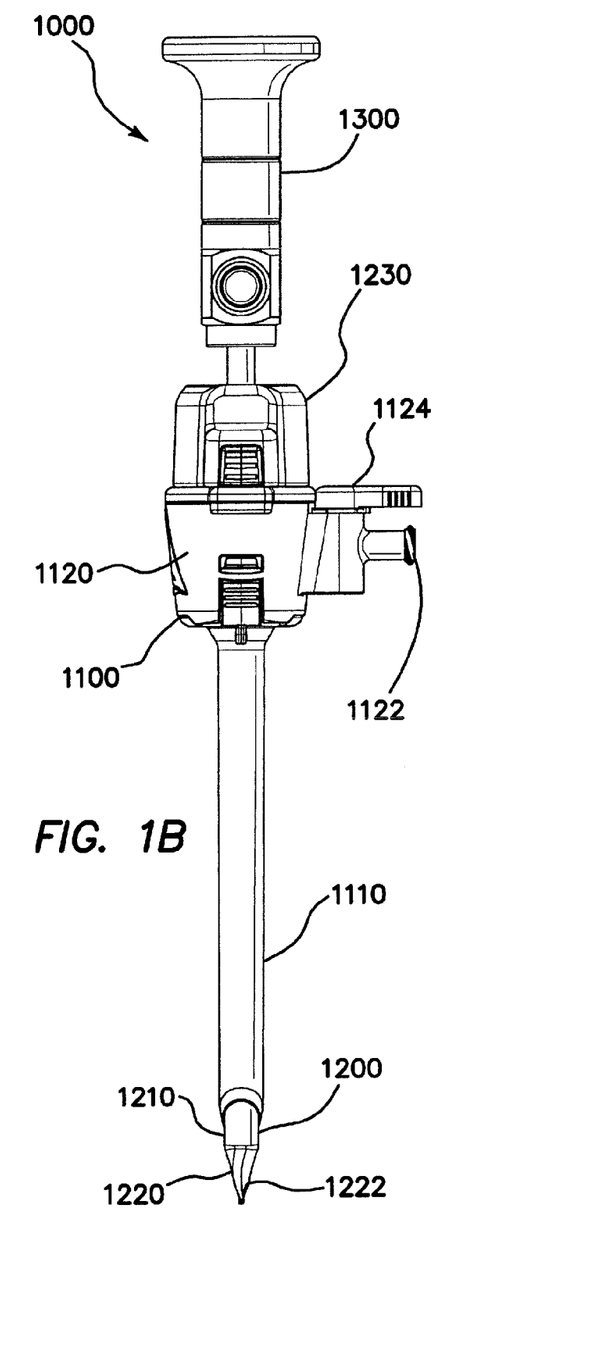

FIGS. 1A and 1B are front and side views of an embodiment of a surgical access or trocar system 1000, which is suitable, for example, as a first entry trocar system. The illustrated embodiment is suitable, for example, as a 5-mm trocar system, as well as for trocar systems of other sizes. The illustrated access system 1000 comprises a trocar 1100, an obturator 1200, and a laparoscope 1300.

The trocar 1100 comprises a longitudinal axis, a proximal end, and a distal end. The proximal end is disposed proximal to a user, for example, a surgeon, during use. Conversely, the distal end is disposed away from the user during use. The obturator 1100 comprises a tubular cannula 1110 and a trocar seal assembly 1120 disposed at the proximal end of the cannula 1110. In the illustrated embodiment, the seal assembly 1120 comprises a fluid inlet comprising a Luer fitting 1122 and a stopcock 1124. In other embodiments, the fluid inlet has a different configuration and/or is disposed on another component, for example, on the obturator 1100.

In the illustrated embodiment, the obturator 1200 is an insufflating optical obturator, as will be described in greater detail below. The obturator 1200 comprises a longitudinal axis, a proximal end, and a distal end. The obturator 1200 comprises an elongate shaft 1210, which is dimensioned for slidable insertion into and removal from the tubular cannula 1110 of the trocar, a tip 1220 disposed at the distal end of the shaft 1210, and a handle 1230 disposed at the proximal end of the shaft 1210. In some embodiments, the obturator tip 1220 is a bladeless tip. In other embodiments, the tip 1220 has another configuration useful for traversing and/or penetrating body tissue, for example, a sharp tip, a pointed tip, a pyramidal tip, a bladed tip, a conical tip, and/or a tip comprising one or more sharp edges or sharpened edges. In other embodiments, the tip 1220 is a radiused blunt tip, which is advantageous for traversing an existing body orifice, and/or relatively soft or fatty tissue.

The trocar 1100 and obturator 1200 independently comprise any suitable material. Those skilled in the art will understand that different components of the trocar 1100 and/or obturator 1200 comprise different materials in some embodiments. Suitable materials include, for example, at least one of a polymer, metal, ceramic, and the like. Suitable polymers include engineering polymers, polycarbonate, polysulfone, PEEK, polyether block amide (PEBAX®), polyester, copolyester, acrylic, and the like. Some embodiments of the trocar 1100 and/or obturator 1100 further comprise a composite, for example, a fiber-reinforced polymer. In some embodiments, a stronger material permits reducing a wall thickness of a component without reducing the strength thereof. For example, some embodiments of a metal or composite obturator shaft 1210 are thinner than a corresponding polymer version, thereby increasing the diameter of a lumen thereof without increasing the outer diameter. As discussed in detail below, increasing lumen diameter improves gas flow through the device.

For example, in some embodiments, obturator shaft 1210 comprises a metal tube, for example, a stainless steel tube, with a polycarbonate tip 1220 insert molded onto the tube. In some embodiments, the metal tube has a wall thickness as thin as about 0.003" (about 0.076 mm). An metal obturator shaft 1210 with an inside diameter of about 0.235" (about 6 mm) and an outside diameter of about 0.241" (about 6 mm) provides an acceptable insufflation gas flow rate. The relationship between gas flow rate and component dimensions and configurations is discussed in detail below.

Embodiments of the cannula 1110 typically comprise a rigid material. Some embodiments of the obturator shaft 1210 comprise a rigid material and/or a flexible material because the obturator shaft 1210 is largely supported by the cannula 1110 during use in some embodiments.

Figure 1C:
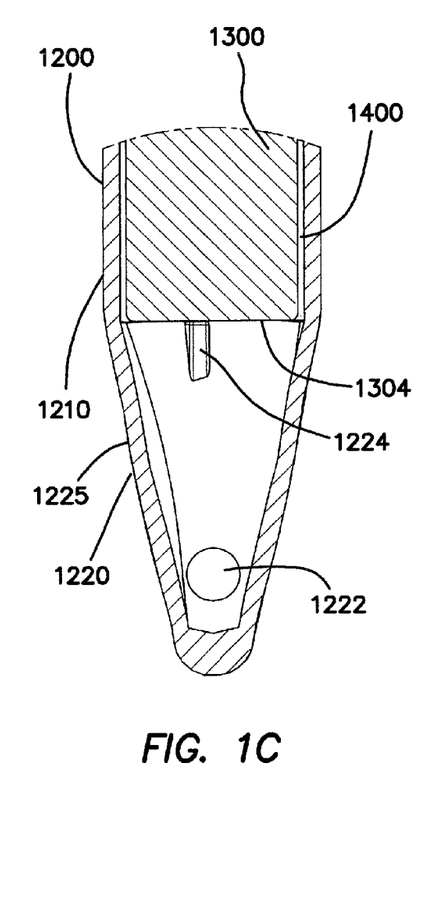
FIG. 1C is a front cross-sectional view and FIG. 1D is a side cross-sectional view a distal end of the insufflating optical obturator illustrated in FIGS. 1A and 1B with a laparoscope inserted therein.
Figure 1D:
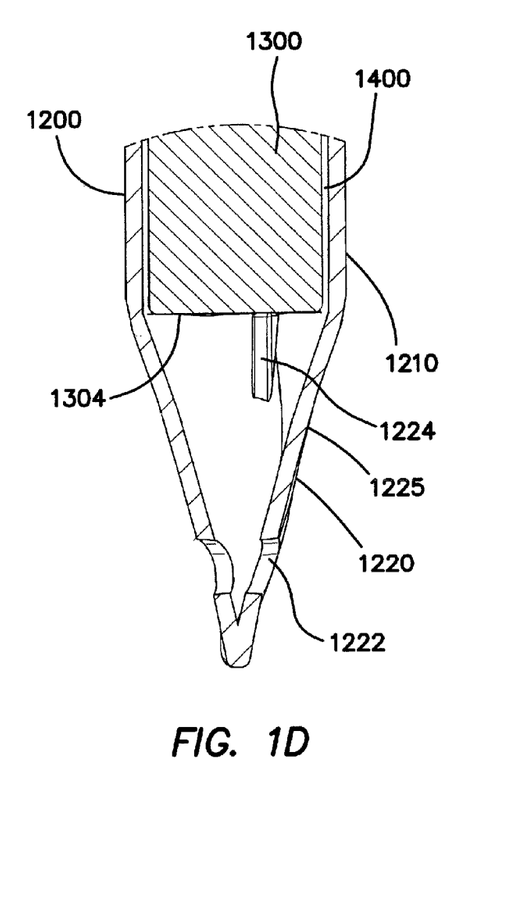

The laparoscope 1300 comprises a proximal end and a distal end 1304 (FIGS. 1C and 1D). The laparoscope 1300 is of any suitable type, for example, comprising an eyepiece at a proximal end and an objective at a distal end thereof. The distal end 1304 of the laparoscope 1300 is dimensioned for slidable insertion into and removal from the obturator shaft 1210.

FIG. 1C is a front cross-sectional view and FIG. 1D is a side cross-sectional view of the distal end of the insufflating obturator 1200 with a laparoscope 1300 inserted therein. The illustrated embodiment depicts a bladeless obturator 1200 suitable for visualization and insufflation therewith. The device include a pair of vent holes 1222 at the distal tip 1220 of the bladeless obturator, through which an insufflating gas, such as carbon dioxide, flows into a body cavity, as discussed in greater detail below. Other embodiments comprise more or fewer vent holes 1222. For example, some embodiments of the tip 1220 of the obturator comprise a single vent hole 1222. In the illustrated embodiment, the vent holes 1222 are generally circular. In other embodiments, the vent holes 1222 have another shape, for example, oval, elliptical, tear-drop shaped, slot shaped, slit shaped, chevron-shaped, triangular, rectangular, rhomboid, polygonal, and the like. In some embodiments, at least one vent hole 1222 has a different shape from another vent hole 1222.

In some embodiments, the obturator 1200 is an optical obturator in which at least a portion of a distal end of the tip 1220 of the bladeless obturator comprises a generally transparent or translucent material, through which tissue is visualized during the insertion of the obturator 1200 through a body wall. Embodiments of the bladeless obturator 1200 are dimensioned and configured to receive therein any suitable laparoscope 1300, which typically includes an imaging element and fiber optic light fibers (not illustrated). The illustrated embodiment of the tip 1220 comprises at least one laparoscope stop 1224, which assists in positioning the laparoscope 1300 within the obturator 1200. In other embodiments one or more laparoscope stops are disposed within the obturator shaft 1210 and/or at the intersection of the shaft 1210 and tip 1220. Other embodiments do not comprise a laparoscope stop.

The illustrated embodiment of the bladeless optical insufflating obturator 1200 includes a tip 1220 configuration comprising one or more features that enhance the visualization and clarity through the tip of the obturator. The illustrated transparent tip 1220 of the obturator through which tissue is observed comprises a wall 1225, at least a portion of which has a substantially uniform thickness. The uniform wall thickness reduces distortion of an image observed through the obturator tip 1220. In some embodiments, the entire obturator tip 1220 comprises a substantially uniform wall thickness. Embodiments of bladeless optical obturators comprising non-uniform wall thicknesses typically exhibit less clear imaging through the obturator tip because the varying wall thickness distorts the image transmitted therethrough, for example, in bladeless optical obturators comprising a generally circular inner contour and a generally rectangular outer contour.

Figure 1E:
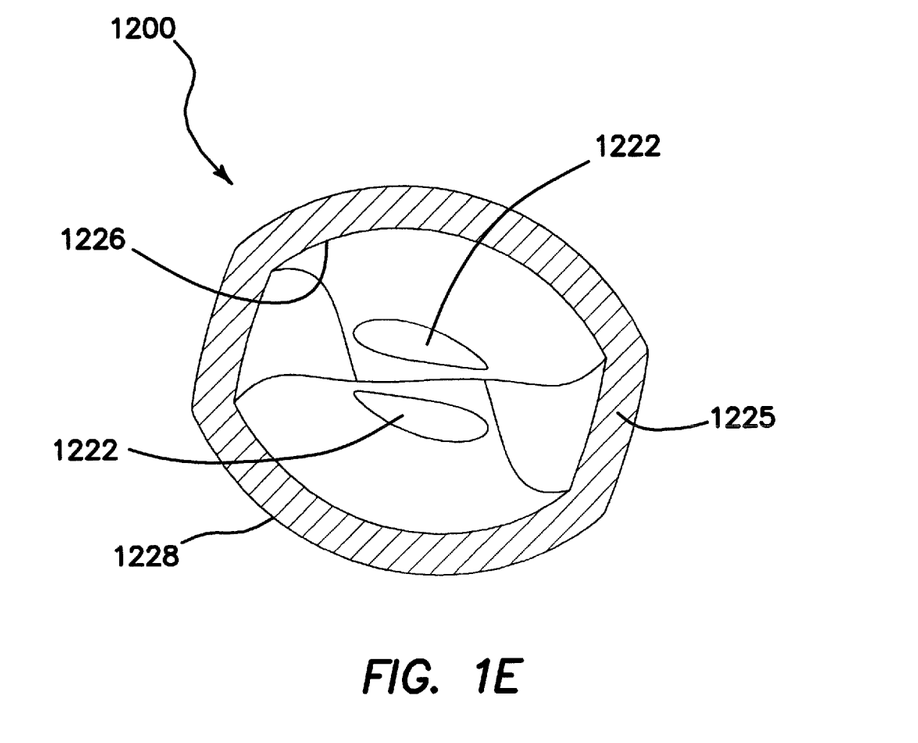
FIG. 1E is a top view of a transverse cross section of a tip of the insufflating optical obturator illustrated in FIGS. 1A-1D.

FIG. 1E is a top view of a transverse cross section of the obturator tip 1220 illustrated in FIGS. 1A-1D. In the illustrated embodiment, an inner contour 1226 of the obturator tip 1220 has a generally rectangular transverse cross section, which substantially matches an outer contour 1228 of the obturator tip, which also has a generally rectangular transverse cross section. In other embodiments, the inner and outer transverse cross-sectional contours 1226 and 1228 of the obturator tip 1220 have another shape, for example, generally elliptical, hexagonal, S-shaped, or another suitable shape. In some embodiments, a portion of an interior surface the tip 1220 at which the distal end laparoscope 1300 contacts has a contour different from a shape or contour of the distal end of the laparoscope. For example, in embodiments in which the distal end of the laparoscope 1300 is circular, the portion of the tip 1220 at which the distal end of the laparoscope 1300 contacts is not circular, thereby defining a gas flow channel therebetween, as discussed in greater detail below.

In some embodiments, at least a portion of the wall 1225 of the obturator tip 1220 comprises a thin-wall configuration. The thin-wall configuration enables light to travel through the material with reduced loss in intensity, thereby enhancing the visibility of tissue through the obturator tip 1220 as the obturator is advanced and placed into the targeted body cavity. The thin-wall configuration also reduces distortion of the image viewed through the obturator tip 1220 and maintains the color accuracy of the viewed tissue. Some embodiments of the obturators 1200 have tip wall thicknesses of from about 0.02" (about 0.5 mm) to about 0.025" (about 0.65 mm) for about 5-mm to 12-mm obturators. In some embodiments, the tip wall is thicker, for example, to provide additional strength.

All transparent materials have a light transmittance value of less than 100%. That is, less than 100% of the light incident on the material is transmitted directly through the material. For a given transparent material, as the wall thickness of the material increases, the amount of light that travels through the material decreases. Moreover, because the illuminating light is directed from within the obturator 1200, the light must travel through the obturator tip 1220 twice, thereby doubling the loss of light due to the transmittance characteristics or absorption of the obturator tip 1220. Embodiments of an obturator tip 1220 with a reduced wall thickness reduce the loss of light or absorption thereby, thereby improving the image of the tissue through which the obturator 1200 is advanced, and maintaining the color accuracy and fidelity of the observed tissue.

In some embodiments, the obturator shaft 1210 and tip 1220 are injection molded as a unitary or single, integral component, which, in combination with the thin-wall tip 1220, allows positioning or placing a distal end 1304 of the laparoscope (FIGS. 1C and 1D) in close proximity to and/or within the tip 1220 of the obturator. By placing the distal end 1304 of the laparoscope in close proximity to and/or within the tip 1220 of the obturator, an image produced through the laparoscope 1300 is magnified compared with an image produced by a distal end 1304 of the laparoscope 1300 positioned at a greater distance from the obturator tip 1220. For example, in some embodiments of a 5-mm bladeless optical obturator designed to accommodate laparoscopes with diameters of from about 5 mm to about 5.5 mm, the distal end of the laparoscope is positionable as close as about 0.442" (about 11 mm) from the distal end of the obturator 1200. Some embodiments of a 12-mm bladeless optical obturator designed to accommodate about 10-mm diameter laparoscopes, permit positioning the distal end of the laparoscope as close as about 0.79" (about 20 mm) from the distal end of the obturator 1200 or less than about 0.83" (about 21 mm) from the distal end of the obturator 1200. In these embodiments, the magnification through the 5-mm optical obturator is greater than that for the 12-mm optical obturator.

The enhanced visibility through the tip 1220 of the obturator also enhances the visibility of the vent holes 1222 in the tip of the obturator. Consequently, in some embodiments, the vent holes 1222 are useful as markers for indicating the penetration depth of the obturator tip 1220. As the surgeon advances the trocar system 1000 through tissue, the surgeon can view the vent holes 1222 through the laparoscope 1300, thereby observing when the vent holes 1222 have traversed a body wall, such as the abdominal wall. Once the vent holes 1222 have traversed a body wall and entered a body cavity, the trocar system 1000 need not be advanced further. Accordingly, the enhanced visibility of the obturator tip 1220 permits precise placement of the access system 1000, and consequently, the trocar 1100 into a body cavity, thereby preventing the trocar 1100 from being advanced too far into the body cavity. Because the surgeon is able to precisely place the trocar system 1000 across a body wall until just the portion of the obturator tip 1200 comprising the vent holes 1222 is positioned within the body cavity, the risk of injury to internal body structures is reduced.

In some embodiments, one or more indicia are provided on at least one vent hole 1222, thereby increasing the utility, visibility, and/or prominence of the vent holes 1222 as depth indicators. For example, in some embodiments, one or more contrasting and/or fluorescent colors are printed in the vent hole 1222 bores.

In some embodiments, one or more marker bands or indicia are disposed proximate to or near at least one vent hole 1222, for example, by printing one or more contrasting or fluorescent marker bands. The enhanced visibility through the tip 1220 of the obturator permits using the marker bands for monitoring the penetration depth of the obturator 1200. For example, in some embodiments, the marker band is highly visible through the laparoscope 1300 as a rectangular band positioned just proximal to the vent holes 1222. In other embodiments, the marker bands have another shape, for example, dots. As a surgeon advances the access system 1000 through the tissue, the surgeon can view the position of the marker band to determine when the vent holes 1222 have traversed a body wall. The enhanced visualization through the obturator tip 1220 enables precise placement of the trocar 1100 into a body cavity, thereby preventing the trocar 1100 from being advanced too far into the body cavity. Precisely placing the access system 1000 across a body wall until just the portion of the obturator tip 1220 with the vent holes 1222 is in the body cavity reduces the risk of injury to internal body structures.

Referring to FIGS. 1C and 1D, some embodiments provide a device comprising an insufflation flow path or channel 1400 defined by an inner wall of the obturator shaft 1210 and the laparoscope 1300. For example, embodiments of a 5-mm bladeless optical trocar with a 5-mm obturator are dimensioned and configured to accommodate laparoscopes with diameters of from about 5 mm to about 5.5 mm (from about 0.197" to about 0.217") with an insufflation flow channel 1400 extending longitudinally through the inside of the obturator between the outside wall of the laparoscope 1300 and the inside wall of the obturator shaft 1210. The insufflation flow channel 1400 is dimensioned to accommodate a suitable flow of an insufflating gas, for example, carbon dioxide. In some embodiments, a cross-sectional area of the insufflation flow channel is at least about 0.0025 $in^2$ (about 1.6 $mm^2$). In the illustrated embodiment, an inside diameter of the obturator shaft 1210 is larger compared with the inside diameter of the obturator shaft of a typical 5-mm optical obturator. Increasing the inside diameter of the obturator shaft 1210 defines a generally cylindrical flow channel 1400 sufficient for insufflation when either a 5-mm or 5.5-mm laparoscope 1300 is inserted into the obturator 1200. In the illustrated embodiment, an outer diameter of the obturator shaft 1210 is also increased. To accommodate the slightly larger obturator shaft 1210, in some embodiments, the inner diameter and outer diameter of the trocar cannula 1110 are also increased compared with typical a 5-mm trocar cannula.

EXAMPLE 1

A polycarbonate insufflating obturator was manufactured in which the inner diameter of the 5-mm insufflating obturator shaft was 0.235" (6 mm), the outer diameter was 0.272" (6.9 mm), and the wall thickness was 0.018" (0.46 mm). The inner diameter of the mating 5-mm cannula was 0.277" (7 mm), the outer diameter was 0.343" (8.7 mm), and the wall thickness of the cannula was 0.033" (0.84 mm). Based on these dimensions, the cross-sectional area of the obturator flow channel with a 5.5 mm laparoscope inserted therein was 0.0064 $in^2$ (4.1 $mm^2$), which provides a carbon dioxide flow rate of about 6 L/min at an insufflator pressure setting of about 1.6-2 KPa (about 12-15 Torr).

EXAMPLE 2 (COMPARATIVE EXAMPLE)

For comparison, a polycarbonate 5-mm bladeless optical trocar designed to accommodate 5-mm to 5.5-mm laparoscopes included an obturator with an inner diameter of 0.219" (5.6 mm), an outer diameter of 0.225" (5.7 mm), and a wall thickness of 0.003" (0.076 mm). The mating cannula for this obturator had an inner diameter of 0.227" (5.8 mm), an outer diameter of 0.287" (7.3 mm), and a wall thickness of 0.03" (0.76 mm). For comparison, the cross-sectional area of the obturator flow channel with a 5.5-mm laparoscope inserted in the obturator was 0.00068 $in^2$ (0.44 $mm^2$), which provides an insufficient flow of carbon dioxide through the device.

EXAMPLE 3

A 5-mm obturator is molded from polycarbonate with an inside diameter of 0.230" (5.8 mm) and a wall thickness of 0.021" (0.53 mm). The carbon dioxide flow rate through this obturator with a 5.5-mm laparoscope inserted therein is about 3.5 L/minute at an insufflator pressure setting of about 1.6-2 KPa (about 12-15 Torr). The increased wall thickness improves the injection molding process for manufacturing the obturator shaft.

The tip 1220 of a bladeless insufflating obturator is designed to separate and dilate tissue and muscle fibers during traversal of a body wall. Because of the dilating and separating properties of a 5-mm insufflating trocar, increasing the outer diameters of the obturator shaft 1210 and the cannula 1110, as compared with typically sized 5-mm bladeless trocars, does not adversely affect the insertion force of the trocar in the illustrated embodiment. The wall thickness of the obturator shaft 1210 is also sufficient to permit injection molding the shaft 1210 and tip 1220 as a single piece, thereby reducing the overall device cost and increasing production capacity.

Figure 2A:
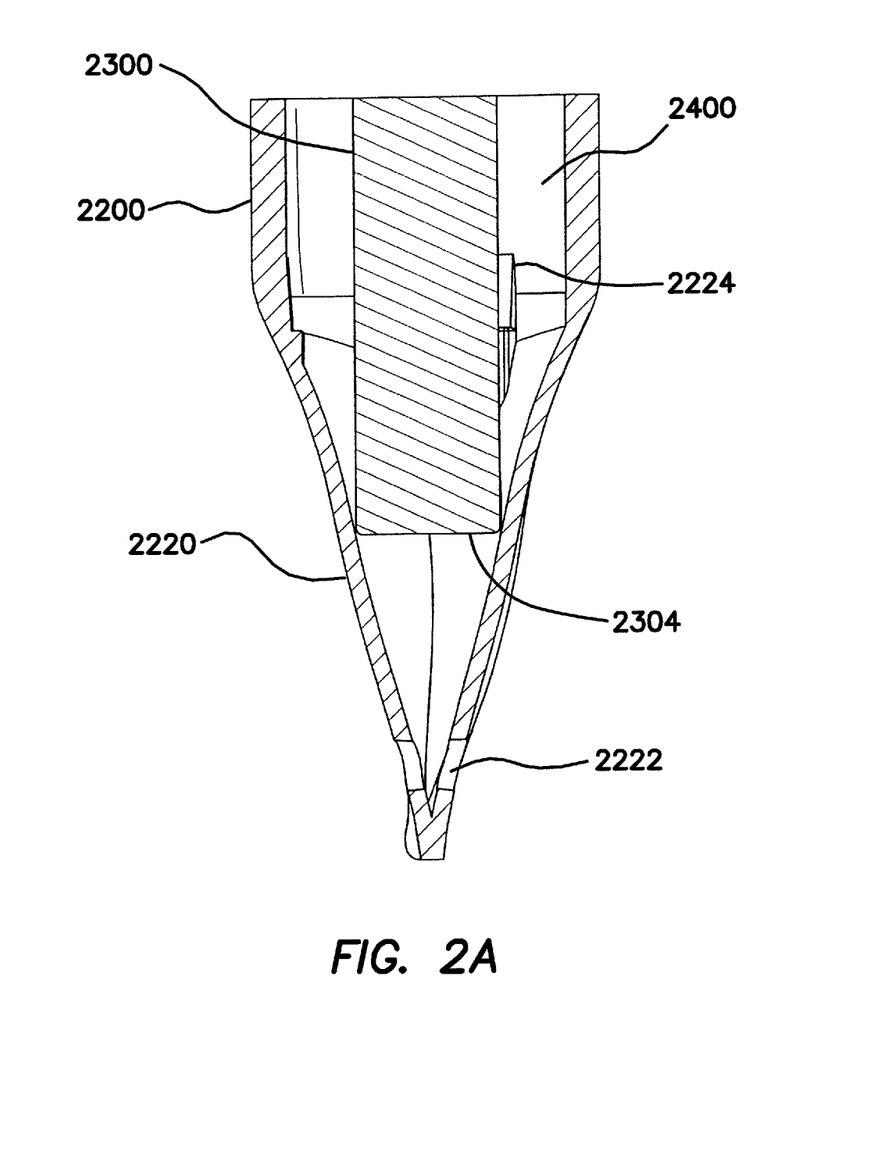
FIG. 2A is a side cross-sectional view and FIG. 2B is a front cross-sectional view of a distal end of another embodiment of an insufflating optical obturator with a laparoscope inserted therein.
Figure 2B:
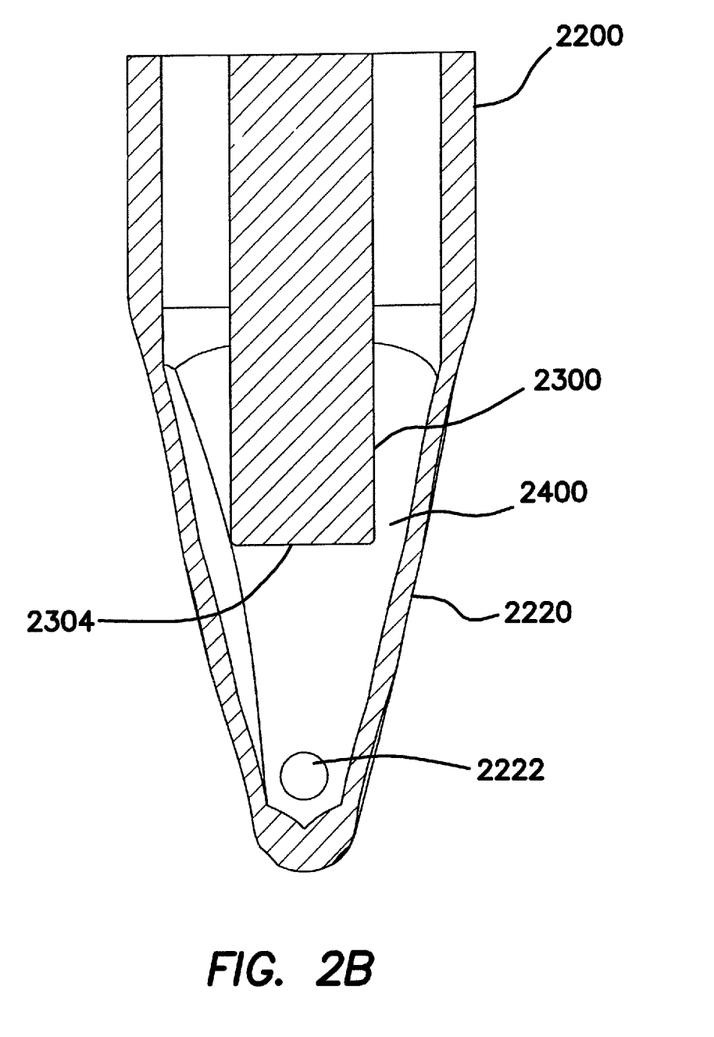
Figure 2C:
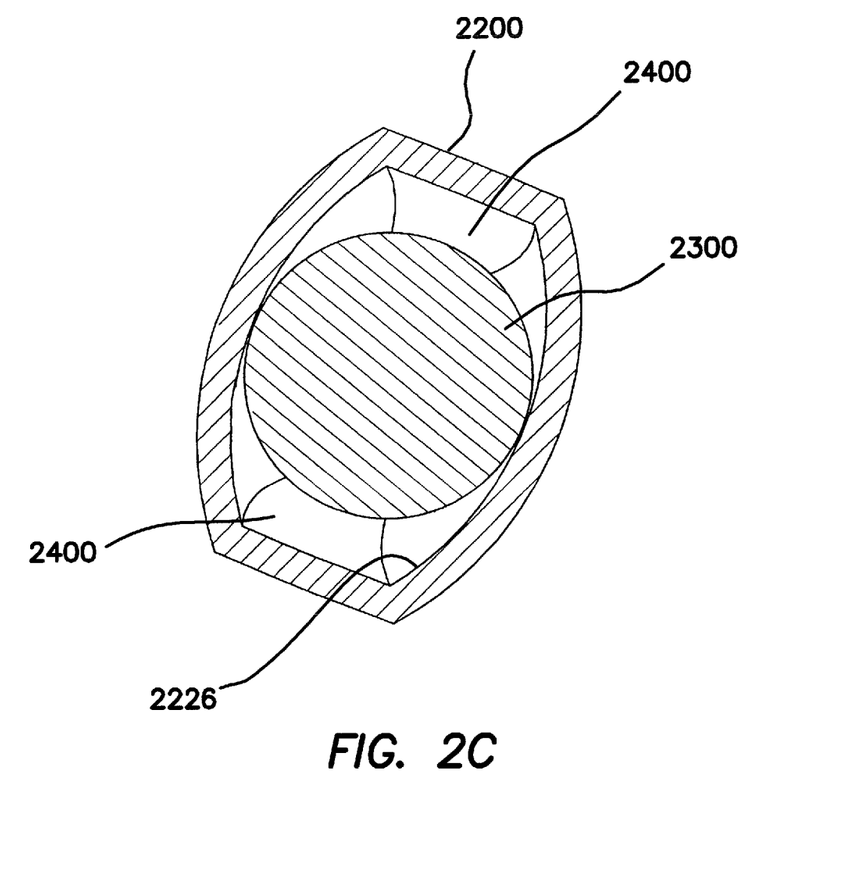
FIG. 2C is a top view of a transverse cross-section of a tip of the insufflating optical obturator and laparoscope illustrated in FIGS. 2A and 2B.

FIG. 2A is a side cross-sectional view and FIG. 2B is a front cross-sectional view of a distal end of another embodiment of an insufflating optical obturator 2200 with a laparoscope 2300 inserted therein. FIG. 2C is a top view of a transverse cross section of a tip 2220 of the insufflating optical obturator 2200 and laparoscope 2300 illustrated in FIGS. 2A and 2B. The following description refers to a 12-mm obturator sized to accommodate 10-mm laparoscopes, which defines an insufflation flow channel sufficient for generating pneumoperitoneum. Those skilled in the art will understand that the illustrated embodiment is also scalable to other size trocar systems.

The illustrated 12-mm obturator also accommodates smaller laparoscopes 2300 such as 5-mm and/or 5.5-mm diameter laparoscopes. The tip 2220 of the obturator is configured such that a distal end 2304 a 5-mm to 5.5-mm laparoscope is insertable deep into a tapered portion of the obturator tip 2220, while still defining an insufflation flow channel 2400 with a sufficient minimum area for a suitable flow of carbon dioxide around the laparoscope 2300. In the illustrated embodiment, a shorter dimension or width of a generally rectangular internal surface 2226 of the tip of the obturator defines a stop for a 5-mm and/or 5.5-mm laparoscope 2300. The insufflation flow channel 2400 is defined by the area between the internal longer dimension or internal length of the internal surface 2226 of the tip and the outside wall of the laparoscope 2300, as best viewed in FIGS. 2A and 2C. The insufflation flow channel 2400 is fluidly connected to one or more vent holes 2222 disposed on the tip. The embodiment illustrated in FIG. 2A also comprises an optional stop 2224 for a 10-mm laparoscope.

Some embodiments in which distal end of the 5-mm or 5.5 mm laparoscope 2300 and the portion of the inner surface 2226 of the tip that acts as a stop therefor have similar shapes do not provide an insufflation flow channel 2400 with an sufficiently large minimum area to provide a desired insufflation gas flow. For example, inserting a round laparoscope 2300 into an obturator 2200 in which the stop portion of the inner surface 2226 has a circular transverse cross section provides only a small or even no flow channel 2400, thereby effectively isolating the vent holes 2222 from the lumen of the shaft 2210 and preventing gas flow therethrough.

The illustrated trocar system exhibits improved flexibility, versatility, and/or performance, while reducing cost and inventory requirements. Pairing a 5-mm and/or 5.5-mm laparoscope with a 12-mm obturator improves the flow rate of carbon dioxide through the obturator 2200 with the laparoscope inserted therein compared with the flow rate through the obturator 2200 with a 10-mm laparoscope inserted therein. Also, a hospital or clinic may not have any 10-mm zero-degree laparoscopes readily available, whereas many facilities have 5-mm and/or 5.5-mm zero-degree laparoscopes readily available. Another advantage is that the distal end of a 5-mm or 5.5-mm laparoscope is closer to the distal end of the obturator tip 2200 compared with a 10-mm laparoscope, thereby providing a magnified image. For example, in the illustrated embodiment, the distal end of a 5-mm or 5.5-mm laparoscope is positioned at about 0.430" (about 11 mm) from the distal end of the tip 2200 of the obturator, while the distal end of a 10-mm laparoscope is positioned at about 0.790" (about 20 mm) from the distal end of the tip 3220 of the obturator.

Figure 3A:
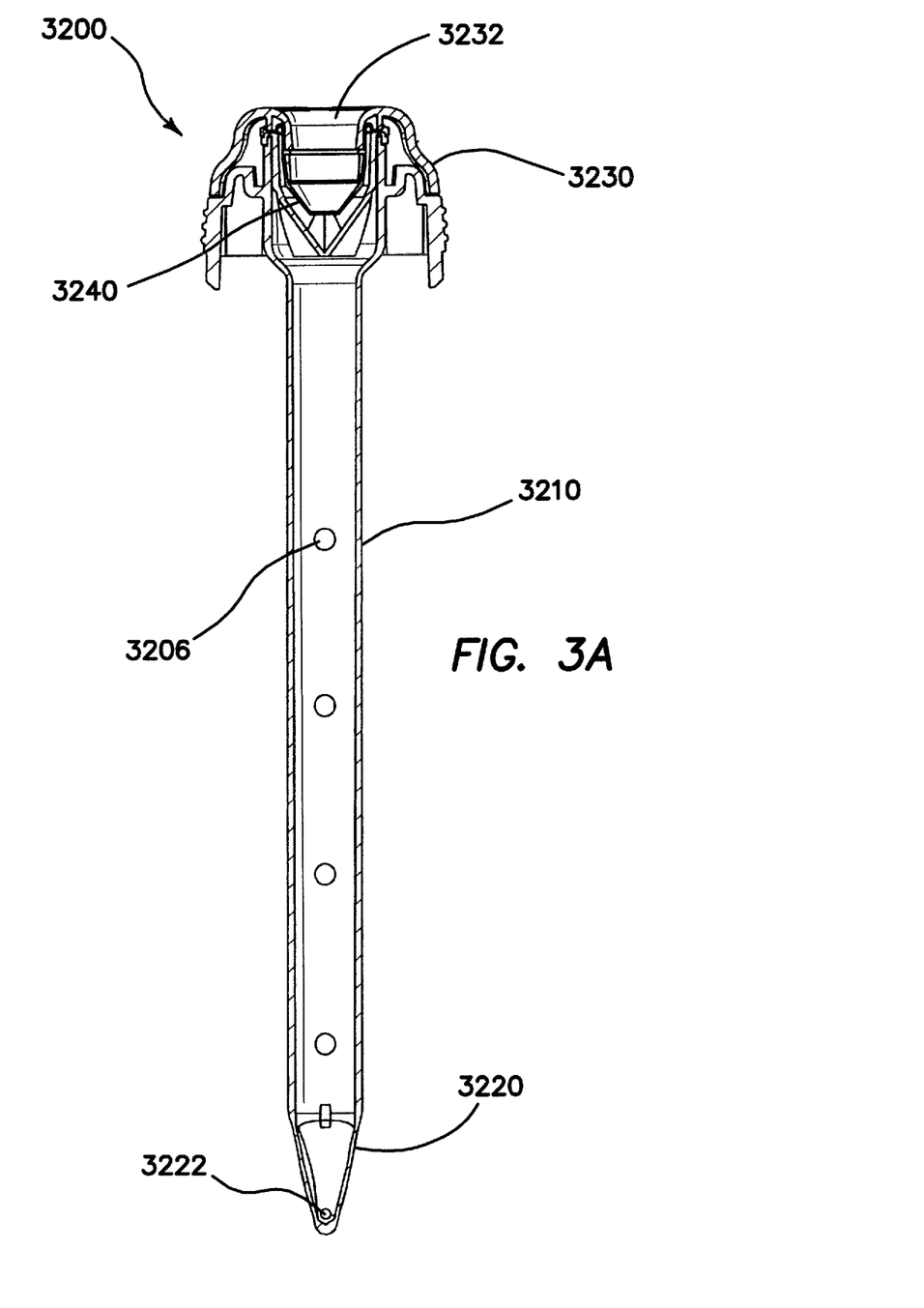
FIG. 3A is a longitudinal cross-section of another embodiment of an insufflating optical obturator.
Figure 3B:
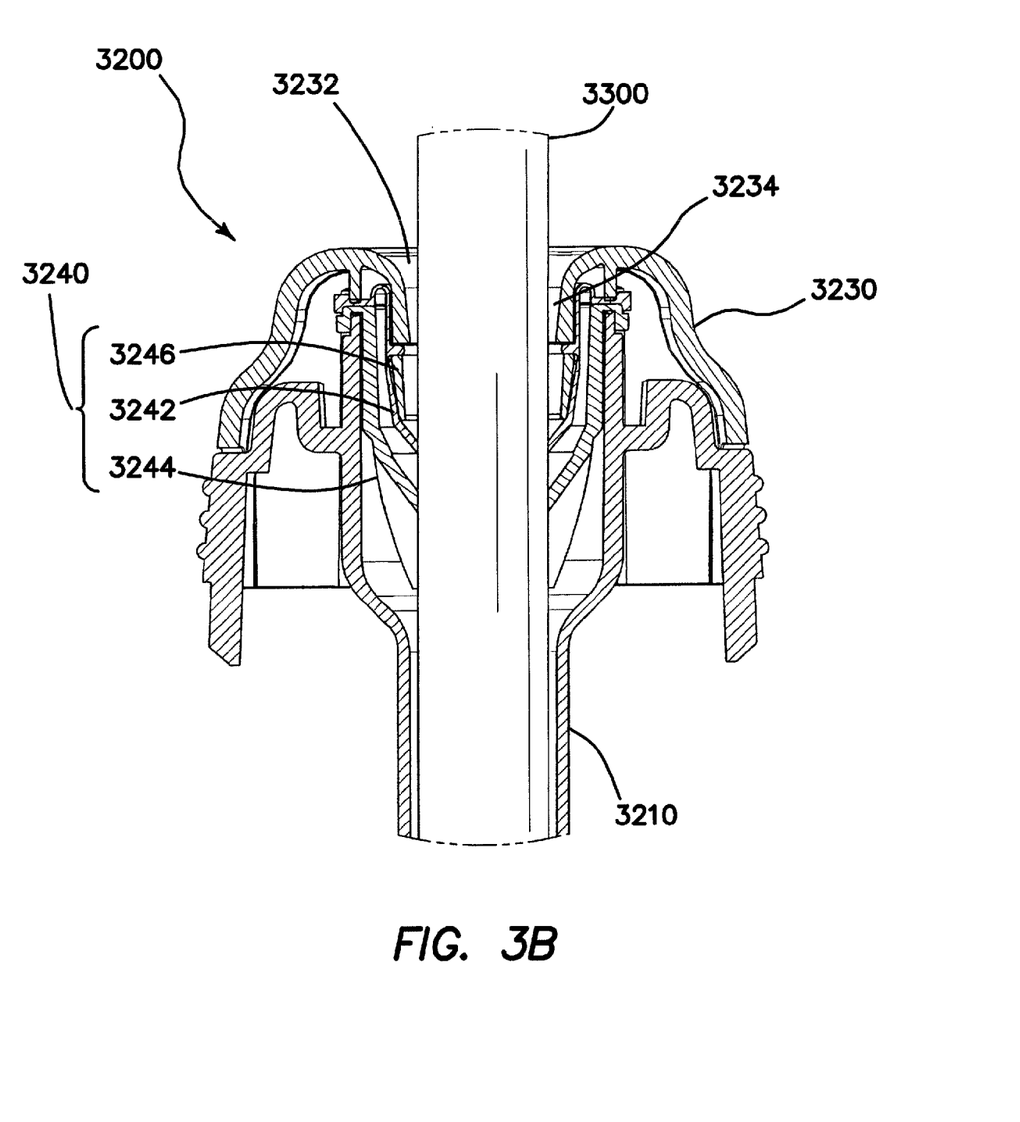
FIG. 3B is a detailed cross section of a handle of the insufflating optical obturator illustrated in FIG. 3A.

FIG. 3A is a longitudinal cross-section of another embodiment of an insufflating obturator 3200 and FIG. 3B is a detailed longitudinal cross section of a proximal end thereof. The insufflating obturator 3200 comprises a shaft 3210, a tip 3220, and a handle 3230. The handle 3230 comprises a funneled entry 3232 disposed at a proximal end thereof. A seal assembly 3240 is disposed distally thereof. Accordingly, the seal assembly 3240 is spaced from and/or recessed from the proximal end of the obturator 3200, thereby encasing the seal assembly 3240 within the handle 3230. Thus, in the illustrated embodiment, the seal assembly 3240 is protected from direct user contact and/or manipulation. In some embodiments in which a seal assembly 3240 is disposed at the proximal end of the obturator 3200 and externally accessible, one or more components of the seal assembly 3240 are vulnerable to inadvertent deformation, for example, during placement of the trocar system, which can cause loss of pneumoperitoneum. Furthermore, in some embodiments, the seal assembly 3240 is vulnerable to deliberate and/or inadvertent removal and/or loss. The illustrated seal assembly 3240 seals with instruments of varying diameters as well as providing a zero seal in the absence of an instrument. Again, using a 12-mm obturator as an illustrative example, the seal assembly 3240 seals with any of 5-mm laparoscopes, 5.5-mm laparoscopes, and/or 10-mm laparoscopes, thereby preventing leakage of carbon dioxide from the proximal end of the obturator 3200.

In the illustrated embodiment of the obturator 3200, at least one opening 3206 perforates the shaft 3210, fluidly connecting the interior or lumen with the exterior thereof. When inserted into a suitable trocar, for example, embodiments of the trocar 1110 illustrated in FIGS. 1A and 1B, the at least one opening 3206 fluidly connects the interior or lumen of the obturator 3200 to the fluid inlet 1122, thereby permitting fluid flow from the fluid inlet 1122, through the openings 3210, and out the vent holes 3222. Some embodiments of the obturator 3200 comprise a single opening perforating the shaft. In some embodiments, the opening or openings 3206 independently have another shape, for example, circular, oval, elliptical, tear-drop shaped, slot shaped, slit shaped, chevron-shaped, triangular, rectangular, rhomboid, polygonal, and the like.

Referring to FIG. 3B, which is a detailed longitudinal cross section of the proximal end of the obturator 3200 illustrated in FIG. 3A, the illustrated seal assembly 3240 comprises an internal septum seal 3242 and an internal duckbill valve 3244 disposed at the proximal end of the obturator shaft 3210. The septum seal 3242 prevents carbon dioxide from leaking from the obturator 3200 when a laparoscope 3300 is inserted therein. The duckbill valve 3244 prevents carbon dioxide from leaking in the absence of a laparoscope 3300, for example, when the laparoscope 3300 is withdrawn from the obturator 3200 or not used at all. The illustrated embodiment also comprises a sleeve 3246 disposed proximally of the septum seal 3242, which prevents and/or reduces inversion of the septum seal 3242 on withdrawal of the laparoscope 3300 therefrom. The septum seal 3242 and the duckbill valve 3444 are disposed between the obturator shaft 3210 and the obturator handle 3230 in the illustrated embodiment. The obturator handle 3230 comprises a funneled entry 3232 at its proximal end leading into a guide channel 3234, which guides or directs the laparoscope 3300 into the obturator 3200. Some embodiments of the obturator handle 3230 comprise a space in the guide channel 3234 sufficient to permit at least some septum seal 3234 inversion during laparoscope 3300 withdrawal without binding the laparoscope 3300. For example, in some embodiments, the diameter of the cap guide channel 3234 is larger than the diameter of the laparoscope plus the thickness of the inverted septum seal, which is sufficient to prevent binding or lock-up of the laparoscope 3300 during withdrawal from the obturator 3200.

In some embodiments, at least one of the septum seal 3242 and duckbill valve 3244 is treated by a chlorination process, which reduces friction when inserting, rotating, and/or withdrawing the laparoscope 3300, which typically has a polished surface that generates high friction with septum seals 3242 and duckbill valves 3244. In some embodiments, at least one of the septum seal 3242 and duckbill valve 3244 is coated or treated with one or more other anti-friction materials and/or coatings, such as silicone oil, silicone emulsion, parylene, polytetrafluoroethylene (Teflon®), and/or treated by plasma etching.

An embodiment of a method for using the surgical access or trocar system refers to the embodiment 1000 illustrated in FIGS. 1A-1E, although the method is applicable to any of the embodiments discussed herein. In the method, the bladeless obturator 1200 is first inserted through the trocar seal 1120 and cannula 1110 of the trocar. A laparoscope 1300 is then inserted into the proximal end of the bladeless obturator 1200 and advanced to the stop 1224 or tip 1220 of the obturator. An endoscopic video camera (not illustrated) is attached to the proximal end of the laparoscope 1300 and the access system 1000 is then axially advanced by a surgeon through a body wall. As the surgeon advances the access system 1000 through the body wall, the surgeon visualizes the tissue as it is being separated, for example, using a video monitor connected to the endoscopic video camera. The surgeon can also readily determine when the body wall has been traversed by observing the distal end of the obturator 1200 entering the body cavity. As discussed above, the distal end of the obturator 1200 includes insufflation vent holes 1222 through which an insufflation gas may flow from the obturator 1200 and into a body cavity.

In another embodiment, the optical access system 1000 accesses a targeted body area or region under laparoscopic guidance as discussed above, then is used to administer a medicament under vision. In some embodiments, the medicament is delivered through the stopcock 1124 and Luer fitting 1122, through the obturator 1200, and out through the vent holes 1222 disposed at the tip 1220 of the obturator. The term "vent hole" is used here for consistency. Those skilled in the art will understand that in some embodiments, gas need not be delivered through the vent holes. Instead, the vent holes are used for another purpose, for example, for delivering a fluid, aspirating a fluid, withdrawing tissue, and/or as a gauge for placing the device, as discussed above. The trocar 1100, in this embodiment, is rigid, semi-rigid, or flexible. Some embodiments of the obturator 1200 comprise a single vent hole 1222. In some embodiments, the vent hole 1222 is disposed at the distal end of the tip 1220, generally along the longitudinal axis of the obturator 1200, which permits a more precise delivery of the medicament. The access system 1000 is suitable, for example, for rapidly accessing a trauma site and for rapidly delivering a medicament through the obturator under vision to the trauma site. In some embodiments, the obturator 1200 is usable in this application either with or without a trocar 1100. In embodiments that do not include a trocar, the obturator 1200 comprises a fluid inlet, for example, a Luer fitting, disposed at or near the proximal end of the obturator 1200, for example, at the handle 1230. The fluid inlet is fluidly connected to the vent hole 1222 through the lumen of the obturator shaft 1210. These embodiments of the trocar system 1100 are also useful for accessing a targeted body area under vision using an inserted laparoscope, then withdrawing a body fluid sample and/or a soft tissue sample through the vent or aspiration hole 1222 of the obturator, for example, for pathology analysis, without a cannula.

In some embodiments, the access system 1000 further comprises an insufflator comprising a gas flow alarm (not illustrated). In some embodiments, a source of insufflation gas, for example, an insufflator, is connected to the Luer fitting 1122, the stopcock valve 1124 opened, and the insufflation gas flow activated, for example, a carbon dioxide flow. When the tip 1220 of the obturator is placed in tissue such as the abdominal wall, the gas flow is blocked by the tissue, which in turn activates a gas flow obstruction alarm of the insufflator. The gas flow obstruction alarm will continue as the trocar is advanced through the tissue until the vent holes 1222 in the tip of the obturator are positioned within a hollow body cavity, at which point, carbon dioxide automatically starts flowing into the cavity and the gas flow obstruction alarm on the insufflator deactivates, thereby serving as an audible indicator that the distal tip 1222 of the obturator is properly positioned within the body cavity.

Some embodiments of the access system 1000 further comprise an integral audible indicator (not illustrated), which indicates gas flow, for example, carbon dioxide, through the device. The audible indicator produces a sound, for example, a high-pitched tone, for example, by mechanically modulating the gas flow through the device. In some embodiments, the audible indicator is disposed in the trocar 1100. In some embodiments in which the audible indicator is integral to the trocar seal 1120, the audible indicator is positioned within and/or integrated with the stopcock Luer fitting 1122. In other embodiments, the audible indicator is disposed in the obturator 1200. In yet other embodiments, the audible indicator is a detachable component, for example, disposed between and fluidly connecting the stopcock Luer fitting 1122 and the insufflation tubing.

In some embodiments, the access system 1000 comprising the audible indicator is connected to an insufflator and the carbon dioxide gas flow activated. When the tip 1220 of the obturator is placed in tissue, such as the abdominal wall, the tissue blocks gas flow through the device. As the tip 1220 is advanced though the tissue, the gas flow remains blocked until the vent holes 1222 in the tip of the obturator reach the targeted body cavity. When the vent holes 1222 are positioned within the body cavity, the carbon dioxide automatically starts flowing into the cavity. The gas flow activates the audible indicator, thereby creating a high-pitched tone, which signals that the distal tip 1220 of the obturator is properly positioned within the body cavity.

Some embodiments of the access system 1000 further comprise a visual indicator (not illustrated), for example, a flow sight that indicates carbon dioxide flow through the device. Suitable visual indicators include a flapper, a rotor, and/or an oscillating ball. In some embodiments, the visual indicator is integral to the trocar seal 1120, for example, positioned within and/or integrated with the stopcock Luer fitting 1122. In other embodiments, the visual indicator is disposed within the proximal portion of the obturator 1200. In other embodiments, the visual indicator is a detachable component disposed between the Luer fitting 1122 and the insufflation tubing.

In an embodiment of a method for using the trocar system comprising the integral visual indicator, the trocar system is connected to an insufflator and the carbon dioxide gas flow activated. When the tip 1220 of the obturator is placed in tissue, such as the abdominal wall, the gas flow is blocked. As the tip 1220 is advanced though tissue, the gas flow remains blocked until the vent holes 1222 in the tip of the obturator enter the targeted body cavity. When the vent holes 1222 are positioned within the body cavity, the carbon dioxide automatically flows into the body cavity. The gas flow causes movement of the visual flow indicator, thereby indicating that the distal tip of the obturator is properly positioned within the body cavity.

Some embodiments of the access system 1000 comprise an electronic gas flow indicator. An output of the gas flow indicator is, for example, audible and/or visible.

While certain embodiments have been particularly shown and described with reference to exemplary embodiments thereof, it will be understood by those of ordinary skill in the art that various changes in form and details may be made therein without departing from the spirit and scope thereof as defined by the following claims.

What is claimed is:

1. A surgical access system comprising:
a tubular trocar comprising a longitudinal axis, a proximal end, a distal end, an elongate cannula, and a seal assembly disposed at a proximal end of the cannula;
an insufflating obturator slidably insertable into the trocar, the obturator comprising a longitudinal axis, a proximal end, a distal end, a tubular shaft, a tapered tip disposed at the distal end of the shaft, at least one vent hole disposed on the tapered tip, the tapered tip having an inner surface and an outer surface, and a handle disposed at the proximal end of the shaft;
a laparoscope; and
a fluid inlet disposed at a proximal end of the access system,
wherein at least a portion of the tapered obturator tip comprises a wall comprising a transparent material with a substantially uniform thickness, the obturator is configured to slidably receive the laparoscope into the tubular shaft of the obturator and extend into the tapered portion of the tip such that the inner surface of the tip abuts an outer surface of the inserted laparoscope while still defining an insufflation gas flow channel between the inner surface of the tip and an outer surface of the inserted laparoscope; the insufflation gas flow channel fluidly connecting the at least one vent hole to the fluid inlet.

2. The surgical access system of claim 1, wherein the seal assembly comprises a septum seal and a duckbill valve.

3. The surgical access system of claim 1, wherein the fluid inlet is disposed on the proximal end of the trocar.

4. The surgical access system of claim 1, wherein the obturator tip is bladeless.

5. The surgical access system of claim 1, wherein the wall of the obturator tip is not greater than about 0.65 mm thick.

6. The surgical access system of claim 1, wherein the obturator tip has an inner contour that is different from the shape or contour of the distal end of the laparoscope.

7. The surgical access system of claim 1, wherein the obturator shaft and tip are unitary.

8. The surgical access system of claim 1, wherein the obturator tip comprises at least one of polymer, polycarbonate, polysulfone, PEEK, polyether block amide (PEBAX®), polyester, copolyester, and acrylic.

9. The surgical access system of claim 1, wherein the obturator tip comprises a single vent hole.

10. The surgical access system of claim 1, wherein the at least one vent hole is at least one of circular, oval, elliptical, tear-drop shaped, slot shaped, slit shaped, chevron shaped, triangular, rectangular, rhomboid, and polygonal.

11. The surgical access system of claim 1, further comprising a depth indicator on the obturator tip.

12. The surgical access system of claim 11, wherein the depth indicator comprises at least one indicia disposed in a bore of the at least one vent hole, and indicia disposed proximate to the at least one vent hole.

13. The surgical access system of claim 1, wherein the obturator further comprises at least one laparoscope stop disposed on at least one of the interior surface of the obturator tip and the interior surface of the obturator shaft.

14. The surgical access system of claim 1, wherein the interior surface of the obturator tip comprises a non-circular transverse cross section.

15. The surgical access system of claim 1, wherein the obturator accommodates laparoscopes with varying diameters.

16. The surgical access system of claim 1, wherein the obturator tip accommodates a distal end of the laparoscope.

17. The surgical access system of claim 1, wherein at least one opening perforates the obturator shaft.

18. The surgical access system of claim 1, wherein a cross-sectional area of the insufflation gas flow channel is at least about 1.6 mm$^2$.

19. The surgical access system of claim 1, wherein a flow rate through the access system is at least about 3.5 L/min at an insufflator pressure of about 1.6-2 KPa.

20. The surgical access system of claim 1 wherein the tip is configured such that the at least one vent hole is located distal to the distal end of an inserted laparoscope.

21. The surgical access system of claim 1 wherein in cross-section perpendicular to the longitudinal axis the outer surface of the tapered tip defines a first shape and the inner surface of the tapered tip defines a second shape that is identical to the first shape.

22. The surgical access system of claim 21 wherein a cross-section of the distal end of the inserted laparoscope taken perpendicular to its longitudinal axis defines a third shape that is different from the first and second shape.

* * * * *